US011203596B2

(12) United States Patent
Silverman et al.

(10) Patent No.: US 11,203,596 B2
(45) Date of Patent: Dec. 21, 2021

(54) ANALOGS OF 3-AMINO-4-(PROPAN-2-YLIDENE)CYCLO-PENTANE-1-CARBOXYLIC ACID AND USES THEREOF FOR TREATING DISEASES AND DISORDERS ASSOCIATED WITH ORNITHINE AMINOTRANSFERASE ACTIVITY

(71) Applicant: Northwestern University, Evanston, IL (US)

(72) Inventors: Richard B. Silverman, Winnetka, IL (US); Matthew J. Moschitto, Evanston, IL (US)

(73) Assignee: Northwestern University, Evanston, IL (US)

( * ) Notice: Subject to any disclaimer, the term of this patent is extended or adjusted under 35 U.S.C. 154(b) by 32 days.

(21) Appl. No.: 16/800,753

(22) Filed: Feb. 25, 2020

(65) Prior Publication Data

US 2020/0299296 A1    Sep. 24, 2020

Related U.S. Application Data

(60) Provisional application No. 62/810,018, filed on Feb. 25, 2019.

(51) Int. Cl.
| | |
|---|---|
| *C07D 471/08* | (2006.01) |
| *C07C 233/03* | (2006.01) |
| *C07C 229/48* | (2006.01) |
| *A61K 9/00* | (2006.01) |

(52) U.S. Cl.
CPC .......... *C07D 471/08* (2013.01); *A61K 9/0053* (2013.01); *C07C 229/48* (2013.01); *C07C 233/03* (2013.01)

(58) Field of Classification Search
CPC .... C07D 471/08; C07C 233/03; C07C 229/48
See application file for complete search history.

(56) References Cited

U.S. PATENT DOCUMENTS

| | | |
|---|---|---|
| 8,211,865 B2 | 7/2012 | Ilan |
| 8,686,041 B2 | 4/2014 | Ilan |
| 8,969,413 B2 | 3/2015 | Silverman |
| 9,603,820 B2 | 3/2017 | Silverman |
| 9,670,141 B2 | 6/2017 | Silverman |
| 9,993,449 B2 | 6/2018 | Silverman |
| 2012/0245380 A1 | 9/2012 | Ilan |
| 2013/0041028 A1 | 2/2013 | Silverman |
| 2015/0196522 A1 | 7/2015 | Silverman |
| 2016/0128958 A1* | 5/2016 | Silverman ............... A61P 43/00 514/561 |
| 2017/0101364 A1 | 4/2017 | Silverman |
| 2017/0239202 A1 | 8/2017 | Silverman |
| 2018/0098952 A1 | 4/2018 | Silverman |
| 2018/0271816 A1 | 9/2018 | Silverman |
| 2019/0315677 A1 | 10/2019 | Silverman |
| 2019/0359555 A1 | 11/2019 | Silverman |

FOREIGN PATENT DOCUMENTS

WO    2016073983 A2    5/2016

OTHER PUBLICATIONS

Moschitto et al. J. Am. Chem. Soc. 2019, 141, 10711-10721 (Year: 2019).*
American Cancer Socitey (2016) "Liver Cancer." Jul. 20, 2016, Accessed online at: http://www.cancer.org/acs/groups/cid/documents/webcontent/003114-pdf.pdf, Jul. 20, 2016.
Brosnan, M. E. et al. "Hepatic Glutamate Metabolism: A Tale of 2 Hepatocytes." Am. J. Clin. Nut. 2009, 90, 857S-861S.
Cadoret, A., et al. "New Targets of B-Catenin Signaling in the Liver Are Involved in the Glutamine Metabolism." Oncogene 2002, 21, 8293-8301.
Christensen, E. M., et al. "Resolving the Cofactor Binding Site in the Proline Biosynthetic Enzyme Human Pyrroline-5-Carboxylate Reductase 1." J. Bio. Chem. 2017.
De Lope, C. R., et al. "Management of Liver Diseases 2012management of Hcc." Journal of Hepatology 2012, 56, S75-S87.
International Searching Authority. International Search Report and Written Opinion for application PCT/US2020/019705, dated May 28, 2020.
Juncosa, J. I., et al. "Design and Mechanism of (S)-3-Amino-4-(Difluoromethylenyl)Cyclopent-1-Ene-1-Carboxylic Acid, a Highly Potent Gamma-Aminobutyric Acid Aminotransferase Inactivator for the Treatment of Addiction." J. Am. Chem. Soc. 2018, 140, 2151-2164.
Juncosa, J. I., et al. "Two Continuous Coupled Assays for Ornithine-Delta-Aminotransferase." Anal. Biochem. 2013, 440, 145-149.
Lee, H., et al. "Mechanism of Inactivation of Gamma-Aminobutyric Acid Aminotransferase by (1s,3s)-3-Amino-4-Difluoromethylene-1-Cyclopentanoic Acid (Cpp-115)." J. Am. Chem. Soc. 2015, 137, 2628-2640.
Liu, W., et al. "Crystal Structures of Unbound and Aminooxyacetate-Bound *Escherichia coli* Gamma-Aminobutyrate Aminotransferase." Biochem. 2004, 43, 10896-10905.
Liu, Y., et al. "Titanium-Mediated Direct Carbon-Carbon Double Bond Formation to ?-Trifluoromethyl Acids: A New Contribution to the Knoevenagel Reaction and a High-Yielding and Stereoselective Synthesis of ?-Trifluoromethylacrylic Acids." Adv. Syn.Cat. 2011, 353, 3161-3165.
Markova, M., et al. "Determinants of Substrate Specificity in Omega-Aminotransferases." J. Biol. Chem. 2005, 280, 36409-36416.
Mascarenhas, R., et al. "Selective Targeting by a Mechanism-Based Inactivator against Pyridoxal 5'-Phosphate-Dependent Enzymes: Mechanisms of Inactivation and Alternative Turnover" Biochem. 2017, 56, 4951-4961.

(Continued)

*Primary Examiner* — Matthew P Coughlin
(74) *Attorney, Agent, or Firm* — Quarles & Brady LLP

(57) ABSTRACT

Disclosed are compound and methods of using the compounds for modulating ornithine aminotransferase (OAT) activity. The disclosed compound are characterized as analogs of 3-amino-4-(propan-2-ylidene)cyclopentane-1-carboxylic acid which may be formulated as therapeutic agents for treating diseases and disorders associated with ornithine aminotransferase (OAT) activity such as hepatocellular carcinoma and other cancers.

20 Claims, 2 Drawing Sheets

(56) References Cited

OTHER PUBLICATIONS

Medina, M. A. "Glutamine and Cancer." J. Nutr. 2001, 131, 2539s-2542s.

Miyasaka, Y., et al. "Analysis of Differentially Expressed Genes in Human Hepatocellular Carcinoma Using Suppression Subtractive Hybridization." Brit. J. Cancer 2001, 85, 228-234.

Moschitto, M. et al. "Mechanism of Inactivation of Ornithine Aminotransferase by (1 S, 3 S)-3-Amino-4-(hexafluoropropan-2-ylidenyl) cyclopentane-1-carboxylic Acid." Journal of the American Chemical Society 141.27 (2019): 10711-10721.

Pan, Y., et al. "Design, Synthesis, and Biological Activity of a Difluoro-Substituted, Conformationally Rigid Vigabatrin Analogue as a Potent Gamma-Aminobutyric Acid Aminotransferase Inhibitor" J. Med. Chem. 2003, 46, 5292-5293.

Ramachandran, P. V., et al. "Bis-Exo-2-Norbornylboron Triflate for Stereospecific Enolization of 3,3,3-Trifluoropropionates." Org. Lett. 2010, 12, 4474-4477.

Shen et al. (1998), "Crystal structure of human recombinant ornithine aminotransferase," J. Mol. Biol. 277 (1):81-102.

Silverman, R. B. "[10] Mechanism-Based Enzyme Inactivators." Methods in enzymology 1995, 249, 240-283.

Silverman, R. B. "Design and Mechanism of Gaba Aminotransferase Inactivators. Treatments for Epilepsies and Addictions." Chem Rev 2018, 118, 4037-4070.

Silverman, R. B. "The 2011 E. B. Hershberg Award for Important Discoveries in Medicinally Active Substances: (1s,3s)-3-Amino-4-Difluoromethylenyl-1-Cyclopentanoic Acid (Cpp-115), a Gaba Aminotransferase Inactivator and New Treatment for Drug Addiction and Infantile Spasms." J. Med. Chem. 2012, 55, 567-575.

Wise, D. R. et al. "Glutamine Addiction: A New Therapeutic Target in Cancer." Trends in Biochemical Sciences 2010, 35, 427-433.

World Health Organization (2014) "World Cancer Factsheet." Jul. 20, 2016, Accessed online at: http://publications.cancerresearchuk.org/downloads/Product/CS_REPORT_WORLD.pdf, Jul. 20, 2016.

Zigmond, E., et al. "Suppression of Hepatocellular Carcinoma by Inhibition of Overexpressed Ornithine Aminotransferase." ACS Med. Chem. Lett. 2015, 6, 840-844.

Zucman-Rossi, J., et al. "Differential effects of inactivated Axin1 and activated β-catenin mutations in human hepatocellular carcinomas." Oncogene 26.5 (2007): 774-780.

* cited by examiner

ANALOGS OF 3-AMINO-4-(PROPAN-2-YLIDENE)CYCLO-PENTANE-1-CARBOXYLIC ACID AND USES THEREOF FOR TREATING DISEASES AND DISORDERS ASSOCIATED WITH ORNITHINE AMINOTRANSFERASE ACTIVITY

CROSS-REFERENCE TO RELATED PATENT APPLICATIONS

The present application claims the benefit of priority under 35 U.S.C. § 119(e) to U.S. Provisional Application No. 62/810,018, filed on Feb. 25, 2019, the content of which is incorporated herein by reference in its entirety.

STATEMENT REGARDING FEDERALLY SPONSORED RESEARCH OR DEVELOPMENT

This invention was made with government support under DA030604 awarded by the National Institutes of Health. The government has certain rights in the invention.

BACKGROUND

The field of the invention relates to new compounds and uses thereof for modulating ornithine aminotransferase activity. In particular, the field of the invention relates to new analogs of 3-amino-4-(propan-2-ylidene)cyclopentane-11-carboxylic acid for inhibiting ornithine aminotransferase activity in diseases and disorders such as cancer.

Liver cancer is the second leading cause of cancer death in men worldwide. Activation of the Wnt/β-catenin signaling pathway, and development in the liver of HCC, correlates with the upregulation of ornithine aminotransferase (OAT), glutamate transporter GLT-1, and glutamine synthetase. OAT converts ornithine and α-ketoglutarate to glutamate-γ-semialdehyde, which subsequently cyclizes to Δ-1-pyrroline-5-carboxylate and glutamate. The produced glutamate is subsequently converted to glutamine, an essential feedstock for rapidly proliferating cells.

Ornithine aminotransferase (OAT) has been found to be overexpressed in liver HCCs. Therefore, inhibiting OAT has been suggested as an innovative treatment for liver cancer and has been shown to be effective in mice. Previously, the compound (1S,3 S)-3-amino-4-(perfluoropropan-2-ylidene) cyclopentane-1-carboxylic acid was shown to be a potent inactivator of human OAT, and administration of this compound to HCC-bearing mice resulted in a decrease in tumor size and the HCC marker protein, alpha-fetoprotein. Here, we described the synthesis of analogs of (1S,3S)-3-amino-4-(perfluoropropan-2-ylidene)cyclopentane-1-carboxylic acid. We show that the analog, (1S,3S,Z)-3-amino-4-(1,1,1-trifluoro-3-methoxy-3-oxopropan-2-ylidene)cyclopentane-1-carboxylic acid in which one trifluoromethyl group has been replaced with a methyl ester, is active against hOAT. Our findings may be applied to devise new treatment therapies for cancers such as liver cancer and hepatocellular carcinoma.

SUMMARY

Disclosed are compounds and methods of using the compounds for modulating ornithine aminotransferase (OAT) activity. The disclosed compounds are characterized as analogs of 3-amino-4-(propan-2-ylidene)cyclopentane-1-carboxylic acid which may be formulated as therapeutic agents for treating diseases and disorders associated with ornithine aminotransferase (OAT) activity such as hepatocellular carcinoma and other cancers.

DETAILED DESCRIPTION

Figure 1:
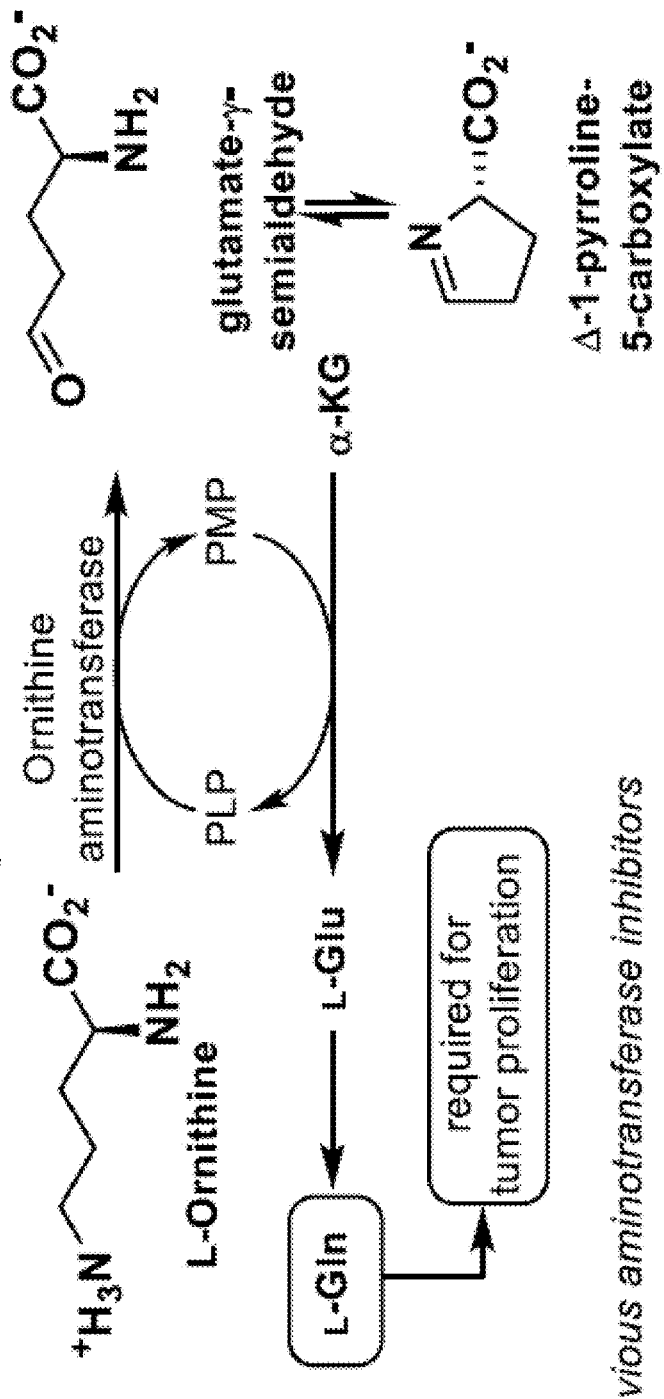
FIG. 1: Catalytic mechanism of hOAT and aminotransferase inhibitors.
Figure 1:
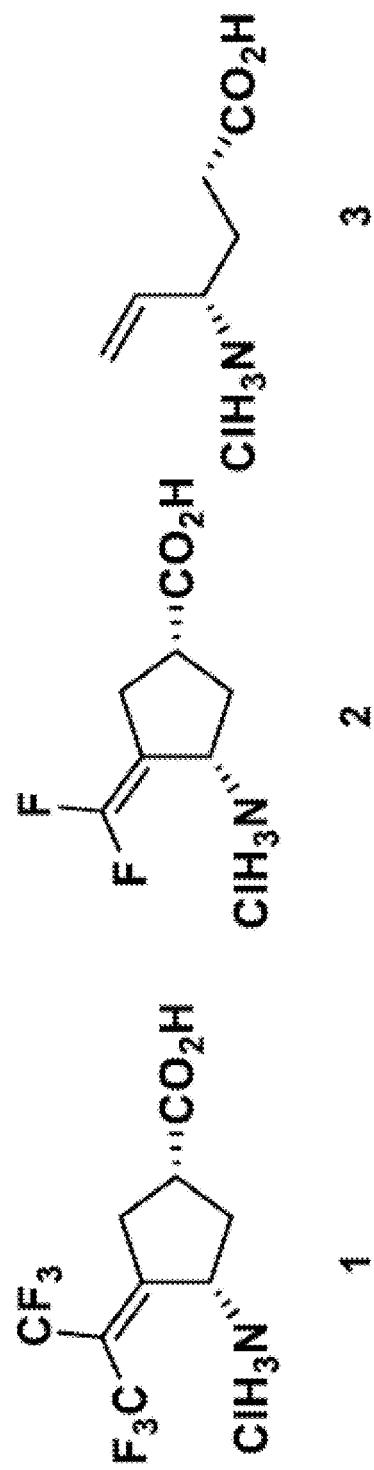

The present invention is described herein using several definitions, as set forth below and throughout the application.

Definitions

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a therapeutic agent" should be interpreted to mean "one or more therapeutic agents." As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or "B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the terms "bind," "binding," "interact," "interacting," "occupy" and "occupying" refer to covalent interactions, noncovalent interactions and steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds. Noncovalent interactions include, but are not limited to, van der Waals interactions, hydrogen bonds, weak chemical bonds (via short-range noncovalent forces), hydrophobic interactions, ionic bonds and the like. A review of noncovalent interactions can be found in Alberts et al., in Molecular Biology of the Cell, 3d edition, Garland Publishing, 1994. Steric interactions are generally understood to include those where the structure of the compound is such that it is capable of occupying a site by virtue of its three dimensional structure, as opposed to any attractive forces between the compound and the site.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

Ornithine Aminotransferase (OAT)

As used herein, the term "ornithine aminotransferase" (OAT) refers to an enzyme that catalyzes a reversible reaction of interconversion between ornithine and a 2-oxo acid to an L-glutamate 5-semialdehyde and an L-amino acid. (See Enzyme Commission number 2.6.1.13). In particular, OAT and catalyzes a reversible reaction of interconversion between ornithine and α-ketoglutarate to Δ-1-pyrroline-5-carboxylate and glutamate. Human OAT is encoded by the OAT gene located on human chromosome 10, which encodes for a protein that is approximately 46 kDa in size. Human OAT is expressed primarily in liver and kidney but also in the brain and the retina. Human OAT is localized in mitochondria. The structure of the human OAT protein has been resolved using X-ray crystallography. (See, e.g., Shen et al. (1998), "Crystal structure of human recombinant ornithine aminotransferase," J. Mol. Biol. 277 (1):81-102; the content of which is incorporated herein by reference in its entirety).

As used herein, the term "modulate" means decreasing or inhibiting and/or increasing or augmenting. For example, modulating ornithine aminotransferase (OAT) activity may mean increasing or augmenting OAT activity and/or decreasing or inhibiting OAT activity. The therapeutic agents disclosed herein may be administered to a subject in need thereof in order to modulate OAT activity, for example in order to inhibit OAT activity wherein the subject has a disease or disorder associated with OAT activity. Ornithine aminotransferase (OAT) activity may be measured using methods disclosed herein and known in the art. (See, e.g., U.S. Published Application Nos. 2018/0098952, 20160128958, and US20120245380; and U.S. Pat. Nos. 8,686,041, and 8,211,865; the contents of which are incorporated herein by reference in their entireties). The compounds disclosed herein may inhibit OAT activity. In some embodiments, the disclosed compounds may function as mechanism based enzyme inactivators (MBEI) of OAT. An MBEI is an inert compound that is converted to an active intermediate by an enzyme's normal catalytic machinery. This active intermediate then can form a covalent bond with the enzyme itself or can bind tightly. (See, e.g., Silverman, R. B. "[10] Mechanism-Based Enzyme Inactivators." Methods in enzymology 1995, 249, 240-283; the content of which is incorporate herein by reference in its entirety). Preferably, the disclosed compounds inactivate OAT with a rate of inactivation ($k_{inact}$) of greater than about 0.01 min$^{-1}$, 0.05 min$^{-1}$, 0.1 min$^{-1}$, 0.15 min$^{-1}$, 0.5 min$^{-1}$, 1.0 min$^{-1}$, 5.0 min$^{-1}$, 10 min$^{-1}$, or higher. Preferably, the disclosed compounds inactivate OAT and have an inhibition constant ($K_I$) of less than about 5 mM, 1 mM, 0.5 mM, 0.1 mM, 0.05 mM, 0.01 mM, 0.005 mM, 0.001 mM, or lower.

Subject in Need Thereof

As used herein, a "subject" may be interchangeable with "patient" or "individual" and means an animal, which may be a human or non-human animal, in need of treatment.

As used herein, the term "a subject in need thereof" refers to a human or non-human subject that can be treated with any of the compounds or pharmaceutical compositions disclosed herein when the compounds or pharmaceutical compositions are utilized as therapeutic agents. A subject in need thereof may include a subject having a disease or disorder that is associated with a biological activity of ornithine aminotransferase (OAT). In some embodiments of the disclosed subject matter, a subject in need thereof may include a subject having a disease or disorder that is associated with increased expression of OAT.

Diseases and Disorders

A subject in need thereof may include a subject having a disease or disorder that is associated with ornithine aminotransferase (OAT), for example a disease or disorder that is associated with expression of OAT (e.g., increased expression of OAT) or a disease or disorder that is associated with a biological activity of OAT (e.g., increased activity of OAT for catalyzing synthesis of glutamate and/or glutamine). Diseases and disorders associated with expression of OAT and diseases or disorders that are associated with a biological activity of OAT are known and may include, but are not limited to cell proliferative diseases or disorders such as cancers. Cancers associated with OAT may include, but are not limited to, liver cancer (e.g., hepatocellular carcinoma (HCC)), cancers such as multiple myeloma, leukemia, non-small cell lung cancer, colon cancer, cancer of the central nervous system, melanoma, ovarian cancer, renal cancer, prostate cancer, breast cancer, and pancreatic cancer.

Therapeutic Agents

As used herein, a "therapeutic agent" may refer to any agent that is administering to a subject in thereof in order to treat the subject. A therapeutic agent may refer to an agent that modulates the biological activity of ornithine amino transferase (OAT) activity, for example where the agent inhibits the biological activity of OAT to catalyze the synthesis of glutamate or glutamine. Therapeutic agents may include, but are not limited to, small molecules or compounds as disclosed herein. Therapeutic agents may include, but are not limited to, pharmaceutical compositions comprising small molecules or compounds as disclosed herein.

Chemical Entities

Chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group (e.g., —(CH$_2$)$_n$— where n is an integer such as an integer between 1 and 20). An exemplary alkylene group is —CH$_2$CH$_2$—.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen.

Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —$R^1$C(O)N($R^2$)—, —$R^1$C(O)N($R^2$)$R^3$—, —C(O)N$R^2R^3$, or —C(O)NH$_2$, wherein $R^1$, $R^2$ and $R^3$, for example, are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "–" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound). The compounds may have an undefined double stereo bond whose substituents may be present in either of the syn-conformation or the anti-conformation (or alternatively in the E-conformation or the Z-conformation).

Use of the Disclosed Compounds as Therapeutic Agents

The disclosed compounds may be formulated as anti-cancer therapeutics, including therapeutics for malignancies such as hepatic malignancies (e.g., hepatocellular carcinoma (HCC)), hematologic malignancies, breast, lung, pancreas, colon, and prostate malignancies.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents.

The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 µM, 0.005 µM, 0.01 µM, 0.5 µM, 0.1 µM, 1.0 µM, 10 µM, and 100 µM (e.g., 0.1 µM-1.0 µM).

The disclosed compounds and pharmaceutical compositions comprising the disclosed compounds may be administered in methods of treating a subject in need thereof. For example, in the methods of treatment a subject in need thereof may include a subject having a cell proliferative disease, disorder, or condition such as cancer (e.g., cancers such as hepatocellular carcinoma (HCC), multiple myeloma, leukemia, non-small cell lung cancer, colon cancer, cancer of the central nervous system, melanoma, ovarian cancer, renal cancer, prostate cancer, breast cancer, and/or pancreatic cancer).

In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds may include doses falling within dose ranges having as end-points any of these disclosed doses (e.g., 2.5 mg-200 mg).

In some embodiments, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds for achieving therapy in the disclosed methods of treatment may include dose levels falling within ranges having as end-points any of these disclosed dose levels (e.g., 500-2000 ng/kg body weight of the subject).

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (Pro-Solv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules. In some embodiments, the compounds are formulated as a composition for administration orally (e.g., in a solvent such as 5% DMSO in oil such as vegetable oil).

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Analogs of 3-Amino-4-(Propan-2-Ylidene)Cyclopentane-1-Carboxylic Acid and Uses Thereof for Treating Diseases and Disorders Associated with Ornithine Aminotransferase Activity The disclosed subject matter relates to new compounds and uses thereof for modulating ornithine aminotransferase activity. In some embodiments, the disclosed subject matter relates to analogs of 3-amino-4-(propan-2-ylidene)cyclopentane-1-carboxylic acid and uses thereof for treating diseases and disorders associated with ornithine aminotransferase (OAT) activity.

In some embodiments, the disclosed compounds have the following Formula I, or dissociated forms, protonated forms, or salts thereof (e.g., HCl salts):

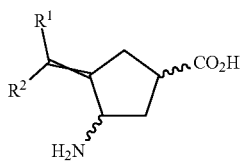

I where: $R^1$ is hydrogen, alkyl (e.g., C1-C6 alkyl which is straight chain or branched), or haloalkyl (e.g., trifluoromethyl); and $R^2$ is carboxyl, carboxylalkyl ester (e.g., carboxylethyl ester or carboxy-t-butyl ester) optionally substituted at one or more positions with halo (e.g., carboxyl-2,2,2-triiodoethyl ester), carboxylaryl ester (e.g., carboxylphenyl ester), carboxylalkylaryl ester (e.g., carboxylbenzyl ester), carboxyl amide, carboxyl-N-alkyl amide (e.g., carboxyl-N-methyl amide), hydroxylalkyl (e.g., hydroxyethyl), aminoalkyl (e.g., aminoethyl), acyl (e.g., acetyl), or cyano.

The disclosed compounds having Formula I may include an undefined double stereo bond at the 4-carbon position of the cyclopentane moiety. The disclosed compounds having Formula I may include E-isomers, and Z-isomers of the In some embodiments, the disclosed compounds may have a Formula Ia:

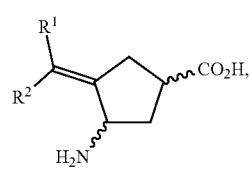

Ia which may be an E-isomer.

In other embodiments, the disclosed compounds may have a Formula Ib:

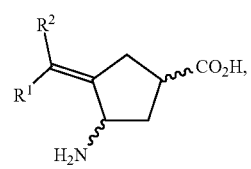

Ib which may be a Z-isomer.

The disclosed compounds may exhibit stereoisomerism at the 1-carbon bearing the carboxyl group, and the 3-carbon bearing the amino group. In some embodiments, the disclosed compounds may have a formula:

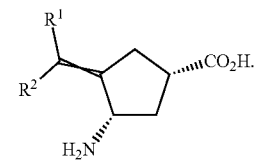

(i.e., a 1S,3S isomer)

In the disclosed compounds, substituent $R^2$ is carboxyl, carboxylalkyl ester optionally substituted at one or more positions with halo, carboxylaryl ester, carboxylalkylaryl ester, carboxyl amide, carboxyl-N-alkyl amide, hydroxylalkyl, aminoalkyl, acyl, or cyano. In some embodiments, substituent $R^2$ comprises a carbonyl group.

In some embodiments, the disclosed compounds may have a formula selected from:

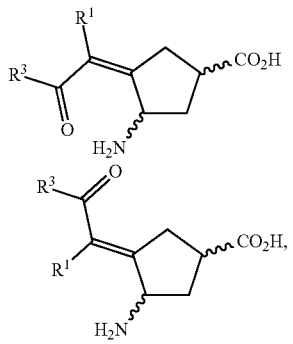

and

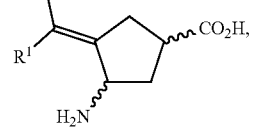

where $R^3$ is hydrogen, hydroxyl, alkyl, alkoxy (e.g., methoxy, ethoxy, or t-butoxy), phenoxy, arylalkoxy, amino, or alkylamino. Specific stereoisomers of the disclosed compounds may include compounds having a formula selected from:

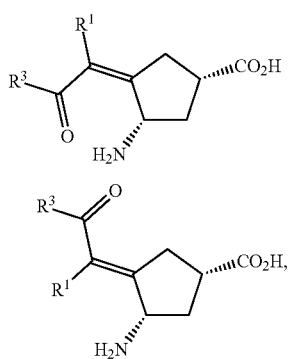

and

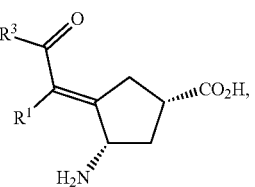

wherein $R^3$ is hydrogen, hydroxyl, alkyl, alkoxy (e.g., methoxy, ethoxy, or t-butoxy), phenoxy, arylalkoxy, amino, or alkylamino.

In some embodiments, the disclosed compounds may have a formula selected from

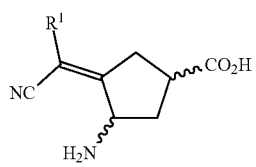 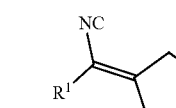

and 

Specific stereoisomers of the disclosed compounds may include compounds having a formula selected from:

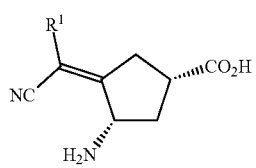 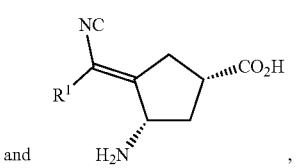

and ,

In some embodiments, the disclosed compounds may include compounds having a formula selected from:

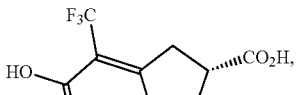

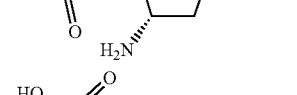

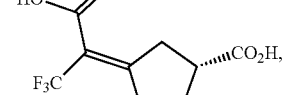

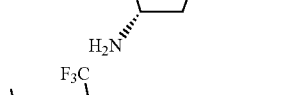

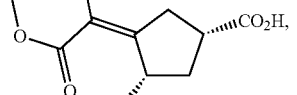

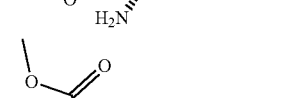

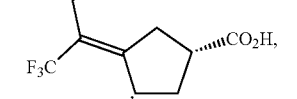

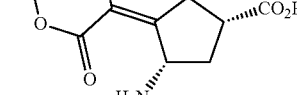

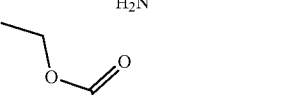

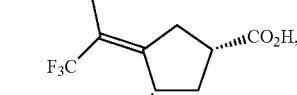

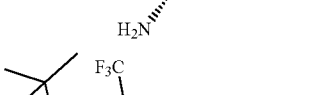

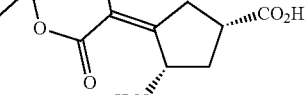

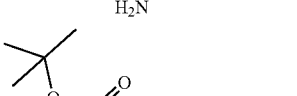

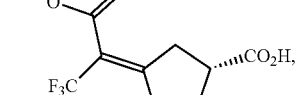

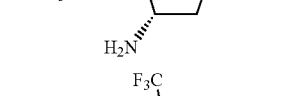

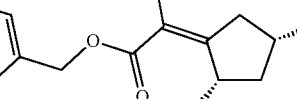

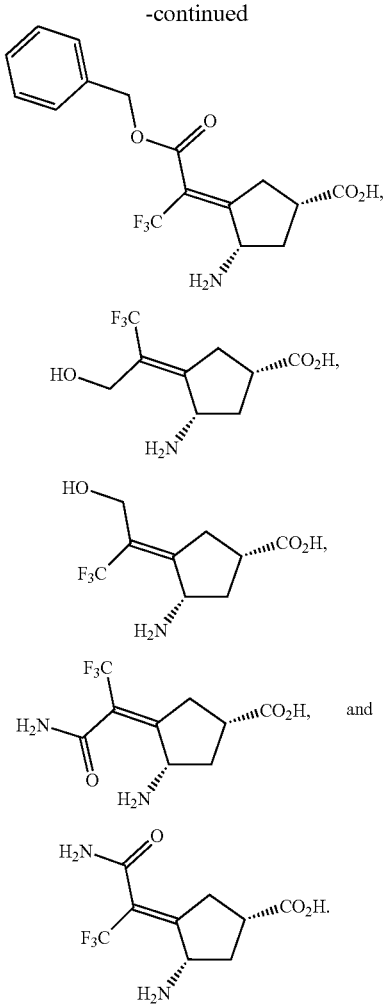

Also disclosed herein are therapeutic agents comprising the disclosed compounds such as pharmaceutical compositions comprising the disclosed compounds. In some embodiments, the disclosed pharmaceutical composition comprise: (i) a compound as disclosed herein; and (ii) a carrier, excipient, or diluent. The disclosed pharmaceutical compositions may comprise an effective amount of the compound for treating a disease or disorder associated with ornithine aminotransferase activity, optionally a cell proliferative disease or disorder associated with ornithine aminotransferase activity, which may include but is not limited to, hepatocellular carcinoma.

Also disclosed herein are method for treating disease or disorders, for example, diseases or disorders associated with ornithine transferase activity in a subject in need thereof, the methods comprising administering to the subject a therapeutic agent (e.g. a compound as disclosed herein or a pharmaceutical composition comprising a compound as disclosed herein). Diseases and disorders treating by the disclosed methods may include, but are not limited to, cell proliferative diseases and disorders such as cancer. Suitable cancers treated by the disclosed methods may include but are not limited to hepatocellular carcinoma. In the disclosed methods, the therapeutic agent may be administered by any suitable method including, but not limited to, orally. In some embodiments of the disclosed methods, the therapeutic agent is a compound or a pharmaceutical composition comprising a compound as disclosed herein, where the compound or the pharmaceutical composition are administered at a dose that delivers to the subject between about 32 mg compound/60 kg subject/day and 200 mg compound/60 kg subject/day.

Also disclosed herein are compounds that may be utilized as precursor compounds for preparing the disclosed compounds. In some embodiments, the precursor compounds have a formula:

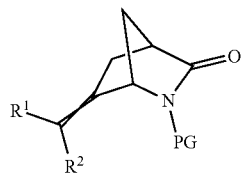

where PG is a protecting group (e.g., an amino protecting group such as p-methoxybenzyl (PMB), 9-fluorenylmethyl carbamate (FMOC), t-butyl carbamate (BOC), benzyl carbamate (Cbz), acetamide (Ac), trifluoroacetamide, phthalimide, benzylamine (Bn), triphenylmethylamine (Tr), benzylideneamine, and p-toluenesulfonamide (Ts)); $R^1$ is hydrogen, alkyl (e.g., C1-C6 alkyl which is straight chain or branched), or haloalkyl (e.g., trifluormethyl); and $R^2$ is carboxyl, carboxylalkyl ester (e.g., carboxylethyl ester or carboxy-t-butyl ester) optionally substituted at one or more positions with halo (e.g., carboxyl-2,2,2-triiodoethyl ester), carboxylaryl ester (e.g., carboxylphenyl ester), carboxylalkylaryl ester (e.g., carboxylbenzyl ester), carboxyl amide, carboxyl-N-alkyl amide (e.g., carboxyl-N-methyl amide), hydroxylalkyl (e.g., hydroxyethyl), aminoalkyl (e.g., aminoethyl), acyl (e.g., acetyl), or cyano.

The disclosed precursor compounds may include an undefined double stereo bond. In some embodiments, the disclosed compounds have a formula:

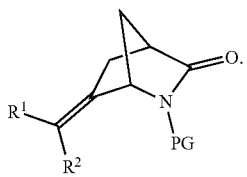

In other embodiments, the disclosed precursor compounds have a formula:

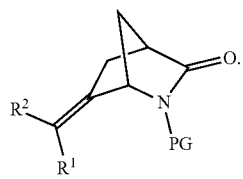

In some embodiments, the disclosed precursor compound may have a formula selected from:
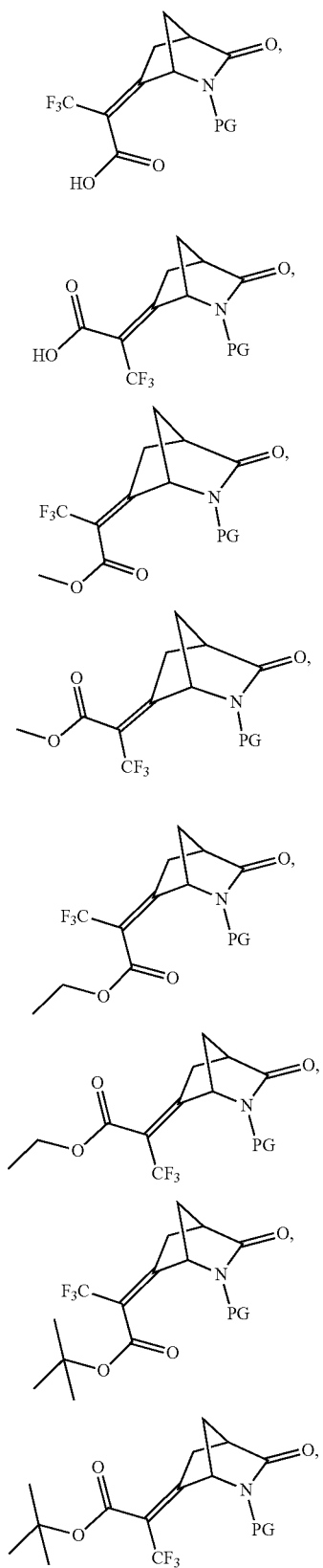
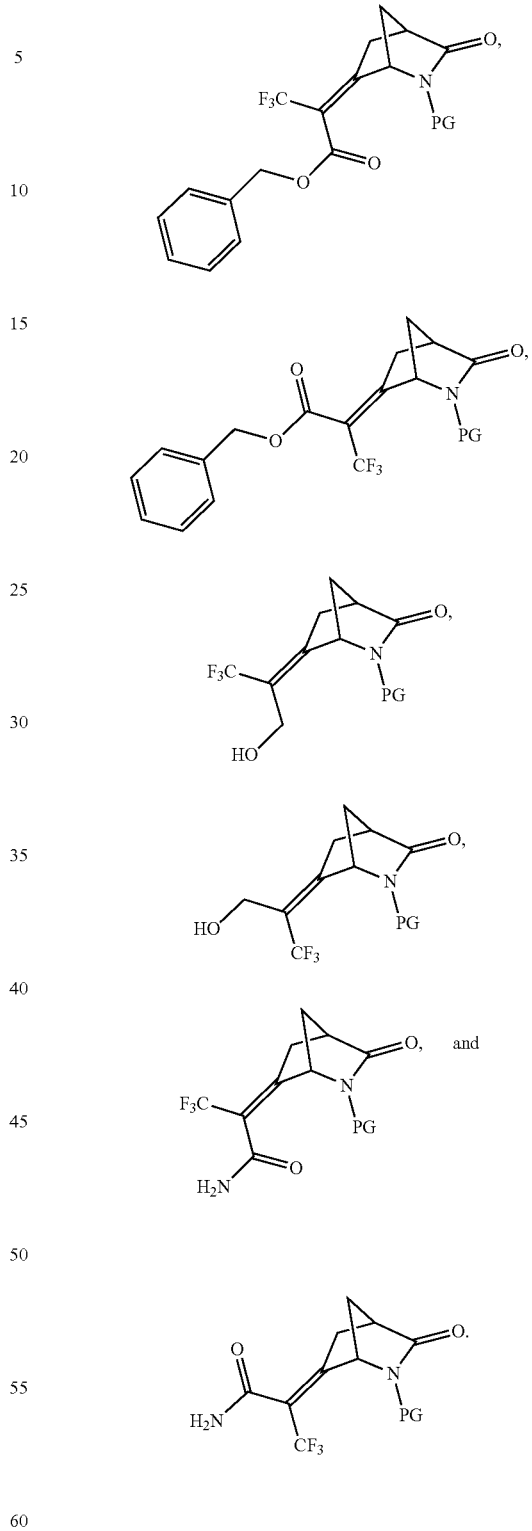
ILLUSTRATIVE EMBODIMENTS
The following embodiments are illustrative and should not be interpreted to limit the scope of the claimed subject matter.

Embodiment 1

A compound having the following formula or a dissociated form, protonated form, or salt thereof:

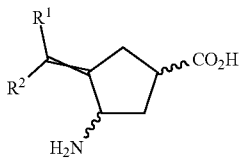

wherein
$R^1$ is hydrogen, alkyl, or haloalkyl; and
$R^2$ is carboxyl, carboxylalkyl ester optionally substituted at one or more positions with halo, carboxylaryl ester, carboxylalkylaryl ester, carboxyl amide, carboxyl-N-alkyl amide, hydroxylalkyl, aminoalkyl, acyl, or cyano.

Embodiment 2

The compound of embodiment 1, wherein $R^1$ is trifluoromethyl.

Embodiment 3

The compound of embodiment 1 having a formula:

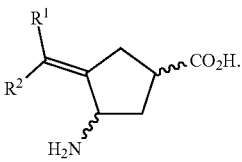

Embodiment 4

The compound of embodiment 1 having a formula:

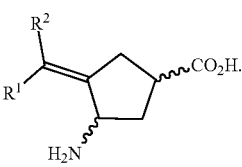

Embodiment 5

The compound of any of the foregoing embodiment having a formula:

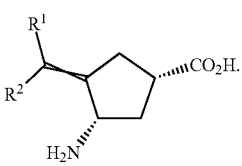

Embodiment 6

The compound of any of the foregoing embodiments having a formula selected from:

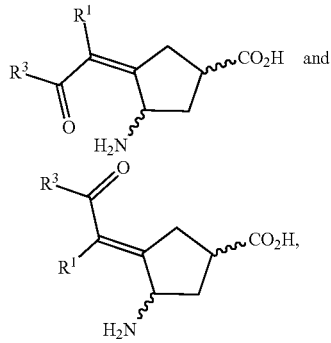

wherein $R^3$ is hydrogen, hydroxyl, alkyl, alkoxy (e.g., methoxy, ethoxy, or t-butoxy), phenoxy, arylalkoxy, amino, or alkylamino.

Embodiment 7

The compound of any of the foregoing embodiments having a formula selected from

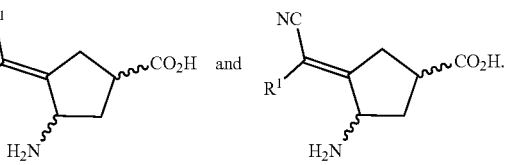

Embodiment 8

The compound of any of the foregoing embodiments having a formula selected from:

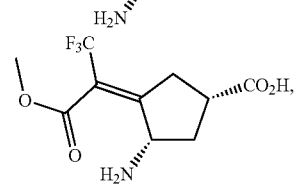

21

-continued

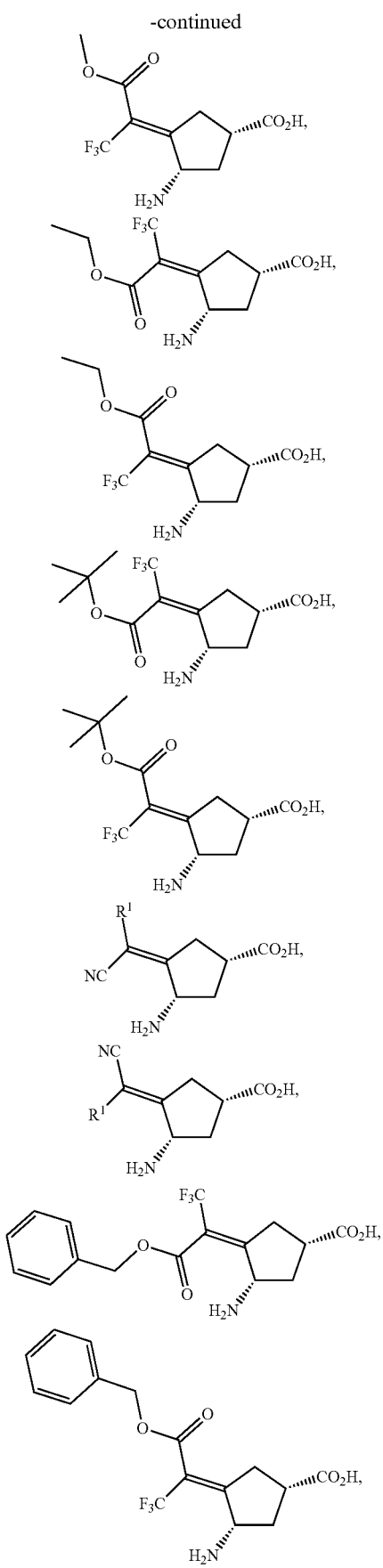

22

-continued

[structures showing compounds with F3C, HO, H2N, CO2H, H2N-C(=O) groups on cyclopentane rings]

and

Embodiment 9

A pharmaceutical composition comprising: (i) a compound of any of the foregoing embodiments; and (ii) a carrier, excipient, or diluent.

Embodiment 10

The pharmaceutical composition of embodiment 9, wherein the pharmaceutical composition comprises an effective amount of the compound for treating a disease or disorder associated with ornithine aminotransferase activity.

Embodiment 11

The pharmaceutical composition of embodiment 9, wherein the pharmaceutical composition comprises an effective amount of the compound for treating a cell proliferative disease or disorder associated with ornithine aminotransferase activity, optionally wherein the cell proliferative disease or disorder is hepatocellular carcinoma.

Embodiment 12

A method for treating a disease or disorder associated with ornithine transferase activity in a subject in need thereof, the method comprising administering to the subject a compound of any of embodiments 1-8 or the pharmaceutical composition of any of embodiments 9-11.

Embodiment 13

The method of embodiment 12, wherein the disease or disorder associated with ornithine transferase activity is cancer.

23

Embodiment 14

The method of embodiment 12 or 13, wherein the disease or disorder associated with ornithine transferase activity is hepatocellular carcinoma.

Embodiment 15

The method of any of embodiments 12-14, wherein the compound or the pharmaceutical composition are administered orally.

Embodiment 16

The method of any of embodiments 12-15, wherein the compound or the pharmaceutical composition are administered at a dose that delivers between about 32 mg compound/60 kg subject/day and 200 mg compound/60 kg subject/day.

Embodiment 17

A compound having a formula

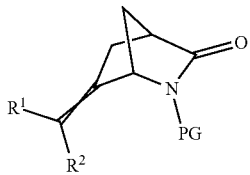

wherein
PG is an amino-protecting group (e.g., p-methoxybenzyl (PMB));
$R^1$ is hydrogen, alkyl, or haloalkyl; and
$R^2$ is carboxyl, carboxylalkyl ester optionally substituted at one or more positions with halo, carboxylaryl ester, carboxylalkylaryl ester, carboxyl amide, carboxyl-N-alkyl amide, hydroxylalkyl, aminoalkyl, acyl, or cyano.

Embodiment 18

The compound of embodiment 17, wherein $R^1$ is trifluoromethyl.

Embodiment 19

The compound of embodiment 17 having a formula:

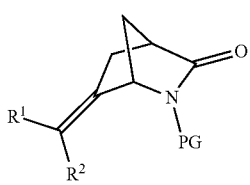

24

Embodiment 20

The compound of embodiment 17 having a formula:

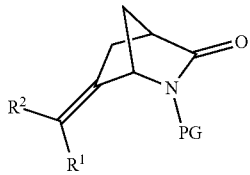

Embodiment 21

The compound of any of embodiments 17-20 having a formula selected from:

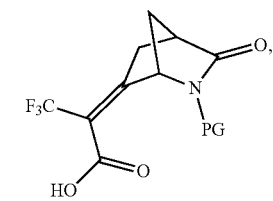

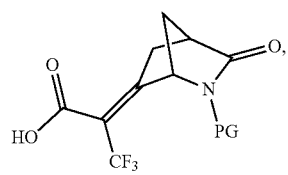

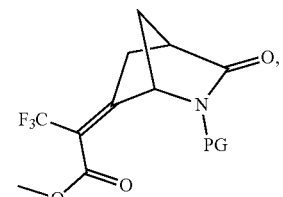

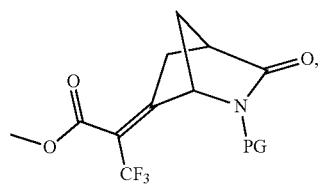

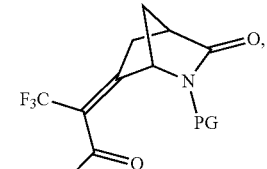

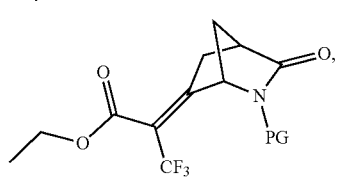

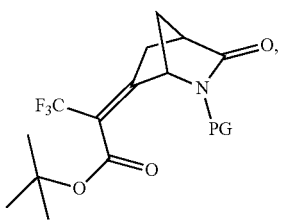

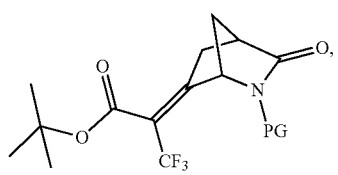

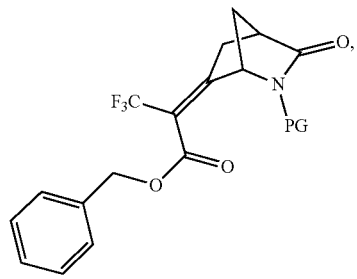

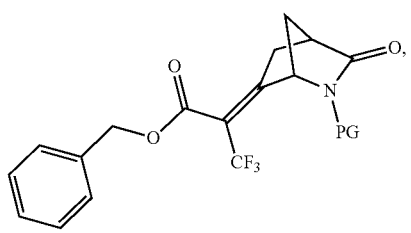

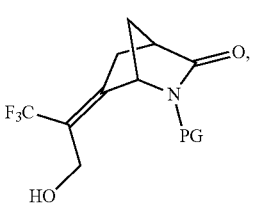

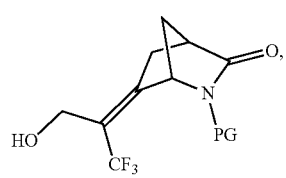

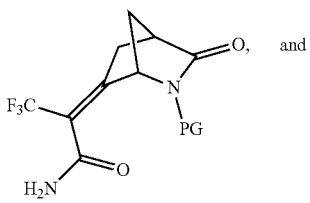

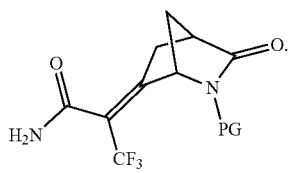

EXAMPLES

The following Examples are illustrative and should not be interpreted to limit the scope of the claimed subject matter.

Synthesis of Substituted Mono-Trifluoromethyl Containing Analogues of (1S,3S)-3-Amino-4-(Perfluoropropan-2-Ylidene)Cyclopentane-1-Carboxylic Acid Hydrochloride for the Inhibition of Ornithine Aminostransferase Liver cancer is the second leading cause of cancer death worldwide.[1] Hepatocellular carcinoma (HCC) accounts for 90% of liver cancer in the United States.[2] Current treatments for liver cancer consist of surgery, radiation, or chemotherapy; however, HCC is highly resistant to both radiation and chemotherapy. Activation of the Wnt/0-catenin signaling pathway, and development in the liver of HCC, correlates with the upregulation of ornithine aminotransferase (OAT), glutamate transporter GLT-1, and glutamine synthetase.[3,4] OAT converts ornithine and α-ketoglutarate to glutamate-γ-semialdehyde, which cyclizes to Δ-1-pyrroline-5-carboxylate, and glutamate (FIG. 1a).[5-7] Glutamate is transported away from the cell (by the GLT-1 transporter) and converted to glutamine by glutamine synthetase. Glutamine is essential for the growth of all cells; tumor cells, however, require enhanced amounts of glutamine to sustain proliferation.[8] Obtaining glutamine from ornithine via OAT provides cancer cells with an alternative source of glutamine that is independent from normal glutamine production. OAT has been found to be overexpressed in liver HCCs; thus inhibiting OAT has been suggested as an innovative treatment for liver cancer and was shown to be effective in mice.[9,10] In 2017, we demonstrated that compound 1 was a potent inhibitor of human OAT, and administration of 1 to HCC infected mice resulted in a decrease in tumor size and the HCC marker protein, alpha-fetoprotein.[9]

Compound 1 was originally designed as an analogue of a potent inhibitor of γ-aminobutyric acid aminotransferase (GABA-AT), CPP-115 (2).[11] CPP-115 is a mechanism based enzyme inactivator (MBEI) of GABA-AT.[12,13] An MBEI is an inert compound that is converted to an active intermediate by an enzyme's normal catalytic machinery. This active intermediate can form a covalent bond with the enzyme itself or can bind tightly. 14 CPP-115 was designed to inactivate GABA-AT by nucleophilic attack on an active site lysine. It was found however, that upon condensation of CPP-115 into PLP and formation of potent Michael acceptor, water hydrolyzed the 1,1-difluoroolefin.[15] This resulted in a dicarboxylate bound to GABA-AT through two electrostatic interactions with two active site arginine residues.

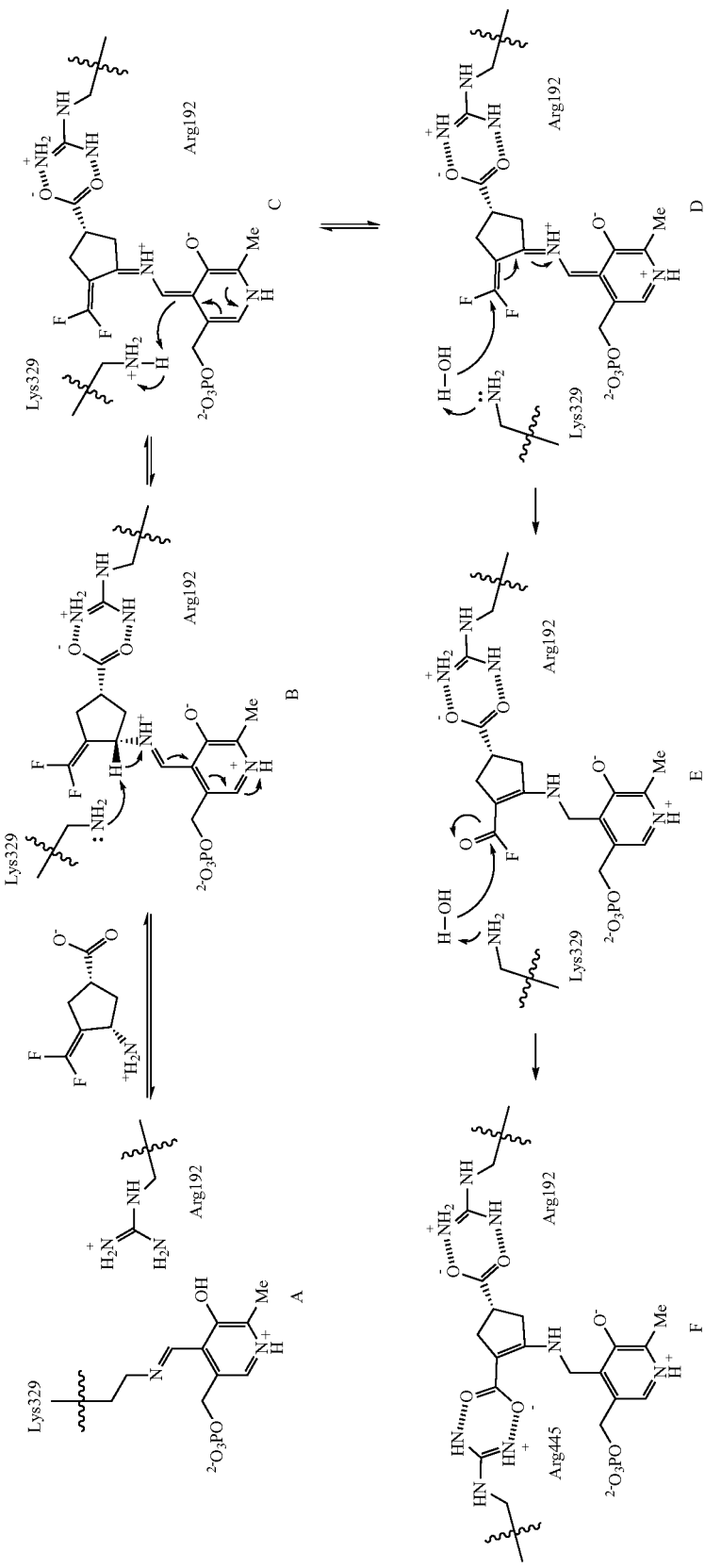
Scheme 1: Mechanism of action of CPP-115 and GABA-AT

Figure 2:
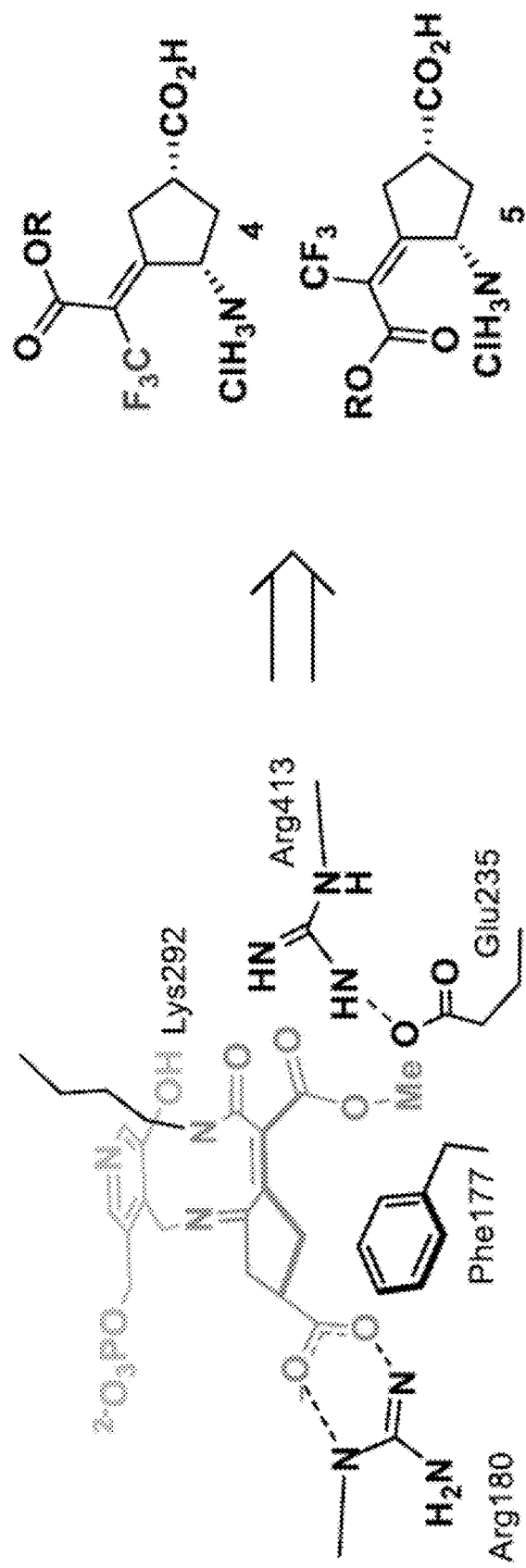
FIG. 2: Development of mono-$CF_3$ ester inhibitors.

We have recently shown that introducing an enone adjacent to the α-nitrogen vastly improves $k_{inact}$.[16] We hypothesized that switching the other trifluoromethyl group to an ester would further lower the pKa of the α-nitrogen proton due to conjugation. Furthermore, when analyzing the active site of hOAT with 1, one notes that there is an arginine and aspartate in the region occupied by second inactive $CF_3$ group. This arginine is known to be flexible and is hypothesized to break its salt bridge with Glu235 upon the binding of α-ketoglutarate.[17,18] Introduction of an extra ester would possibly provide for additional electrostatic interactions with the enzyme, thus increasing $K_1$ (FIG. 2). We therefore proposed a series of syn and anti mono-trifluoro ester and acid compounds as shown in FIG. 2 (4 and 5).

We first focused on the addition of methyl 3,3,3-trifluoropropionate into ketone 6. Although methyl 3,3,3-trifluoropropionate had been used in the Knoevenagel Condensation with aldehydes using various Lewis acids, its use with ketones was less prevalent.[19,20] Exposure of ketone 6 and methyl 3,3,3-trifluoropropionate to $Bu_2BOTf$ cleanly results in addition; however, elimination of the alcohol was not possible. When $TiCl_4$ (2 equiv.) was used, followed by addition of triethylamine, a mixture of isomers 7 and 8 was obtained in modest yield. Careful chromatography was able to separate 7 and 8. Deprotection of the p-methoxybenzyl group with ceric ammonium nitrate, followed by hydrolysis yielded pure 10.

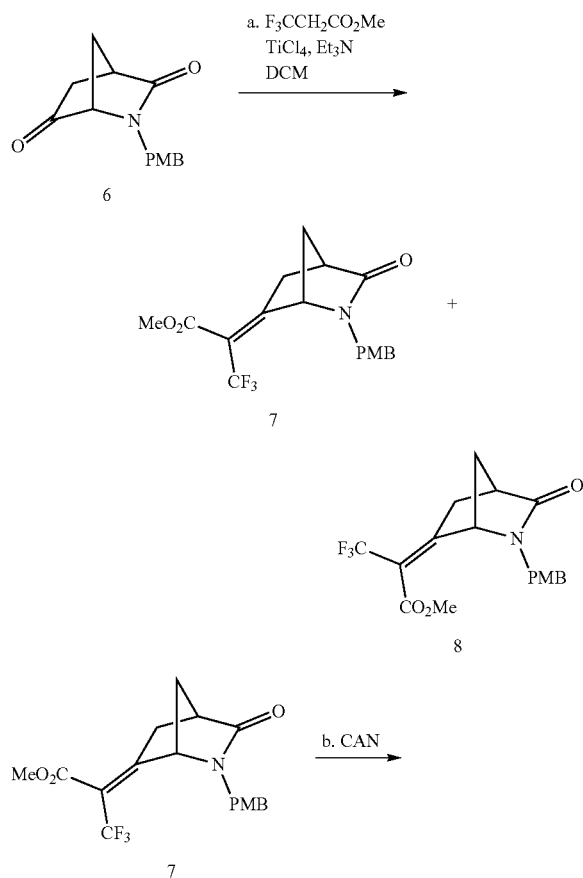

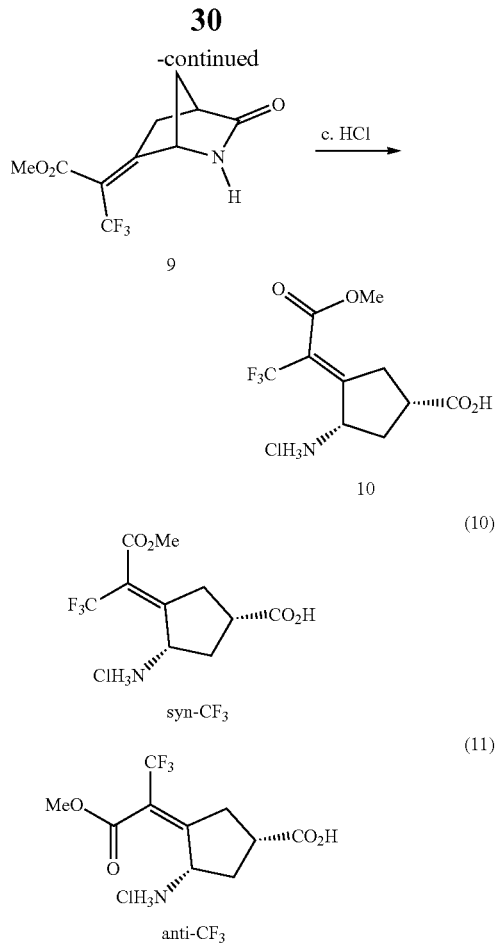

With inhibitors in hand, we tested for activity in a previously developed coupled enzyme hOAT assay.[9,21]

TABLE 1

Kinetic constants and half-life for trifluoromethyl-ester inhibitors

| | $CF_3$ | $K_I$ (mM) | $k_{inact}$ (min$^{-1}$) | $k_{inact}/K_I$ (mM$^{-1}$ min$^{-1}$) |
|---|---|---|---|---|
| 1 | — | 0.053 | 0.08 | 1.54 |
| 10 | syn | 0.13 | 0.10 | 0.73 |
| 11 | anti | ≥2.0 | — | — | trans-Methyl ester 10 proved to be a similarly potent inhibitor of hOAT. The $k_{inact}$ increased slightly when compared to that of 1 (0.10 min$^{-1}$ for 10 versus 0.08 min$^{-1}$ for 1). $K_I$, however, was almost two times less potent for 10 when compared to 1 (0.13 mM versus 0.0.5 mM). This could indicate that the methyl ester is sterically too large for the active site, and thus the binding is slightly reduced. The anti-$CF_3$ ester (11) was shown to be inactive against hOAT.

To obtain the acid and other possible esters, 3,3,3-trifluoropropionate trichloroethyl ester can be used in place of methyl 3,3,3-trifluoropropionate. The resulting mixture of syn and anti esters (13 and 14) is inseparable by chromatography. Deprotection of the trichloroethyl ester with zinc leads to the corresponding acids (15), which are separable. Both isomers can be coupled to various alcohols to gain esters such as ethyl, benzyl, or tert-butyl ester compounds (16). Additionally the acid can be coupled to ammonia to yield an amide (17) or reduced to the alcohol (18). All compounds are then deprotected and hydrolyzed.

Scheme 3: Synthesis of ester, acid amide, and alcohol containing compounds

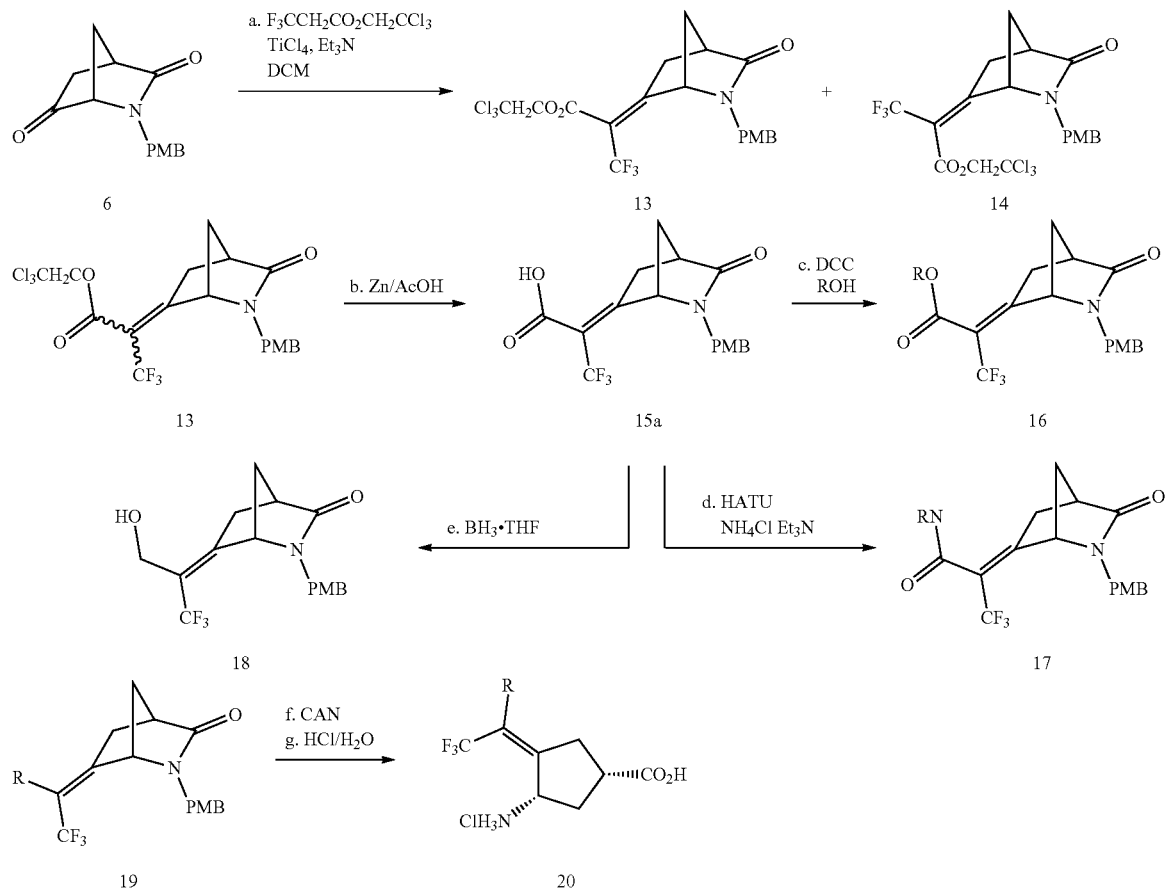

Methods

General Methods hOAT and PYCR1 were expressed, grown, and purified according to literature procedures.[22,23] GABA-AT was isolated from pig brains and purified according to literature procedure.[16] Coupled enzyme assays for GABA-AT and hOAT were carried out according to previous procedures.[15,21] All chemical were purchased from Sigma Aldrich, Acros Organics, or Matrix Scientific and used without further purification. Anhydrous solvents (THF, $CH_2Cl_2$, DMF) were purified before use by passing through a column composed of activated alumina and a supported copper redox catalyst. Yields refer to chromatographically and spectroscopically ($^1$H-NMR) homogeneous material. Analytical thin-layer chromatography (TLC) was performed using Merck Silica Gel 60 Å F-254 precoated plates (0.25 mm thickness), and components were visualized by ultraviolet light (254 nm) and/or ceric ammonium molybdate stain. Flash column chromatography was performed on a Teledyne Combiflash Rf Plus automated flash purification system with various Teledyne cartridges (4-80 g, 40-63 μm, 60 Å). Purifications were performed with hexanes and ethyl acetate unless otherwise noted. $^1$H and $^{13}$C NMR spectra were recorded on a Bruker Avance-III NMR spectrometer at 500 MHz and 126 MHz, respectively, in $CDCl_3$ or $D_2O$. Chemical shifts were reported in ppm, multiplicities are indicated by s=singlet, d=doublet, t=triplet, q=quartet, sep=septet, dd=doublet of doublet, dt=doublet of triplet, m=multiplet, br=broad resonance. Coupling constants were reported in Hz. High resolution mass spectral data were obtained on an Agilent 6210 LC-TOF spectrometer in the positive ion mode using electrospray ionization with an Agilent G1312A HPLC pump and an Agilent G1367B autoinjector at the Integrated Molecular Structure Education and Research Center (IM-SERC), Northwestern University. Analytical HPLC was performed by using a reserved-phase Agilent Infinity 1260 HPLC with a Phenomenex Kintex C-18 column (50×2.1 mm, 2.6 μm), detecting with UV absorbance at 254 nm.

Synthesis of Inhibitors

Methyl(Z)-3,3,3-trifluoro-2-((1S,4S)-2-(4-methoxybenzyl)-3-oxo-2-azabicyclo[2.2.1]heptan-6-ylidene)propanoate (7)

Ketone 612 (140 mg, 0.57 mmol) and methyl 3,3,3-trifluoropropionate (0.075 mL, 0.68 mmol, 1.2 equiv) were dissolved in $CH_2Cl_2$ (3 mL) and cooled to 0° C. $TiCl_4$ (1.1 mL, 1.14 mmol, 2 equiv, 1 M solution in $CH_2Cl_2$) was added slowly. The reaction was stirred for 3 hours at room temperature and then $Et_3N$ (0.40 mL, 2.85 mmol, 5 equiv) was added. The reaction was further stirred for 18 hours and then washed with 1 M HCl (2 mL), dried over $Na_2SO_4$, and concentrated to yield a black oil, which is purified via column chromatography to yield a mixture of 7 (20 mg, 0.054 mmol, 10% yield) and 8 (20 mg, 0.054 mmol, 10%)

as a white solid. The ratio (and yield) of 7 can be increased by shortening the reaction time at each step to 1 h. 7: $^1$H NMR (500 MHz, CDCl$_3$) δ 7.25 (m, 2H), 6.96 (m, 2H), 4.90 (d, J=15.1 Hz, 1H), 4.74 (p, J=1.5 Hz, 1H), 3.93 (s, 3H), 3.89 (s, 3H), 3.65 (d, J=15.2 Hz, 1H), 3.07 (dd, J=1.8, 3.5 Hz, 1H), 2.93 (m, 2H), 2.17 (ddt, J=1.8, 3.7, 10.3 Hz, 1H), 1.71 (dt, J=1.6, 10.5 Hz, 1H). $^{13}$C NMR (126 MHz, CDCl$_3$) δ 176.8, 163.3, 160.4, 159.2, 129.3, 128.3, 122.2 (d, J=274.3 Hz), 117.9 (q, J=32.2 Hz), 114.1, 60.6 (q, J=4.2 Hz), 55.3, 52.5, 43.4, 40.6, 35.6. HRMS (ESI) calc'd for C$_{18}$H$_{19}$F$_3$NO$_4$ (M+H$^+$): 370.1266, found: 370.1256. 8: $^1$H NMR δ 7.25 (d, J=8.6 Hz, 2H), 6.93 (m, 2H), 5.06 (d, J=1.7 Hz, 1H), 4.69 (d, J=15.0 Hz, 1H), 3.99 (d, J=15.0 Hz, 1H), 3.87 (s, 3H), 3.85 (s, 3H), 3.05 (dt, J=1.5, 3.5 Hz, 1H), 2.79 (m, 2H), 2.14 (d, J=10.4 Hz, 1H), 1.65 (dd, J=1.6, 10.2 Hz, 1H). $^{13}$C NMR (126 MHz, CDCl$_3$) δ176.8, 163.1, 159.5 (d, J=2.4 Hz), 159.2, 129.3, 128.8, 122.5 (d, J=274.5 Hz), 118.7 (q, J=32.7 Hz), 114.0, 61.7, 55.3, 52.5, 44.0, 43.9, 40.2, 33.6. HRMS (ESI) calc'd for C$_{18}$H$_{19}$F$_3$NO$_4$ (M+H$^+$): 370.1266, found: 370.1256.

Methyl(Z)-3,3,3-trifluoro-2-((1S,4S)-3-oxo-2-azabi-cyclo[2.2.1]heptan-6-ylidene)propanoate (9)

7 (665 mg, 1.80 mmol) was dissolved in MeCN (9 mL) and cooled to 0° C. Ceric ammonium nitrate (3.0 g, 5.40 mmol, 3 equiv) in 3 mL H$_2$O was added dropwise, and the reaction was stirred for 2 hours. Upon completion, the reaction was diluted with H$_2$O (5 mL) and extracted with ethyl acetate (2×10 mL). After drying over Na$_2$SO$_4$ and concentration, the yellow oil was purified by column chromatography to yield 9 (100 mg, 0.4 mmol, 22% yield) as a white powder. $^1$H NMR (500 MHz, CDCl$_3$) δ 5.6 (s, 1H), 4.8 (m, 1H), 3.8 (s, 3H), 2.9 (s, 1H), 2.8 (q, J=2.2 Hz, 2H), 2.2 (dt, J=10.3, 2.0 Hz, 1H), 1.7 (dq, J=10.4, 1.7 Hz, 1H). $^{13}$C NMR (126 MHz, CDCl$_3$) δ 179.4, 163.2, 161.8 (q, J=2.0 Hz), 117.5, 58.0 (q, J=4.0 Hz), 52.5, 43.2, 41.3, 34.7. HRMS (ESI) calc'd for C$_{10}$H$_{11}$F$_3$NO$_3$ (M+H$^+$): 250.0691, found: 250.0670.

(1S,3S,Z)-3-amino-4-(1,1,1-trifluoro-3-methoxy-3-oxopropan-2-ylidene)cyclopentane-1-carboxylic acid hydrochloride (10)

9 (100 mg, 0.40 mmol) was dissolved in 4 M HCl in dioxane (1 mL) and H$_2$O (1 mL) and heated at 70° C. for 1 hour. After concentration, the solid was recrystallized from EtOH/Et$_2$O to yield 10 (90 mg, 0.30 mmol, 74% yield). $^1$H NMR (500 MHz, D$_2$O) δ 4.79 (m, 1H), 3.82 (s, 3H), 3.15 (m, 3H), 2.49 (dt, J=8.4, 15.3 Hz, 1H), 2.23 (dt, J=4.5, 14.9 Hz, 1H). $^{13}$C NMR (126 MHz, D$_2$O) δ 179.2, 164.3, 157.9, 122.4 (m), 53.4, 52.3, 40.9, 37.1, 33.6. HRMS (ESI) calc'd for C$_{10}$H$_{13}$F$_3$NO$_4$ (M+H$^+$): 268.0797, found: 268.0765.

(1S,3S,E)-3-amino-4-(1,1,1-trifluoro-3-methoxy-3-oxopropan-2-ylidene)cyclopentane-1-carboxylic acid hydrochloride (11)

11 was prepared from 8 in a method similar to above in a 17% yield (two steps). $^1$H NMR (500 MHz, D$_2$O) δ 3.83 (s, 3H), 3.16 (m, 3H), 2.52 (dt, J=7.8, 15.0 Hz, 1H), 2.13 (dt, J=6.3, 13.9 Hz, 1H). 13C NMR (126 MHz, D$_2$O) δ 178.5, 164.4, 161.8, 122.8 (q, J=32.8 Hz), 54.0, 53.5, 41.5, 36.3 (d, J=3.5 Hz), 32.5. HRMS (ESI) calc'd for C$_{10}$H$_{13}$F$_3$NO$_4$ (M+J$^+$): 268.0797, found: 268.0766.

(Z)-3,3,3-trifluoro-2-((1S,4S)-2-(4-methoxybenzyl)-3-oxo-2-azabicyclo[2.2.1]heptan-6-ylidene)propanoic acid (15a)

An inseparable mixture of 13 and 14 was obtained in 16% yield followed the procedure for the synthesis of 7. The mixture of 13 and 14 (570 mg, 1.17 mmol) were dissolved in AcOH (6 mL) and activated Zn dust (150 mg, 2.34 mmol, 2 equiv.) was added. The reaction was stirred for 2 h, filtered and concentrated. The corresponding acids were purified by reverse phase chromatography (water/acetonitrile) to yield syn-CF$_3$ (15a; 270 mg, 0.76 mmol) and anti-CF$_3$ (15b; 48 mg, 0.135 mmol) in 65 and 11%, respectively. $^1$H NMR (500 MHz, CD$_3$OD) δ 7.26 (d, J=8.6 Hz, 2H), 6.85 (d, J=8.6 Hz, 2H), 5.10 (d, J=1.7 Hz, 1H), 4.53 (d, J=14.7 Hz, 1H), 4.00 (d, J=14.8 Hz, 1H), 3.76 (s, 3H), 2.88 (dd, J=1.8, 3.9 Hz, 1H), 2.75 (dt, J=3.6, 17.6 Hz, 1H), 2.46 (dp, J=3.4, 17.7 Hz, 1H), 1.89 (ddt, J=1.8, 3.8, 10.3 Hz, 1H), 1.44 (dd, J=1.5, 10.2 Hz, 1H). $^{13}$C NMR (126 MHz, CD$_3$OD) δ 178.3, 169.6, 159.17, 151.9, 129.2, 129.2, 123.5 (q, J=273.6 Hz), 123.1 (q, J=29.0, 31.4 Hz), 113.5, 62.6, 54.2, 44.1, 43.4, 39.6. HRMS (ESI) calc'd for C$_{17}$H$_{16}$F$_3$NNaO$_4$ (M+Na$^+$): 378.0929, found: 378.0913.

REFERENCES

1. World Health Organization (2014) "World Cancer Factsheet." Jul. 20, 2016, Accessed online at: http://publications.cancerresearchuk.org/downloads/Product/CS_REPORT_WORLD.pdf, Jul. 20, 2016.
2. American Cancer Society (2016) "Liver Cancer." Jul. 20, 2016, Accessed online at: http://www.cancer.org/acs/groups/cid/documents/webcontent/003114-pdf.pdf, Jul. 20, 2016.
3. J., Z.-R., B. S., G. C., S. Boyault, G. G., C. Balabaud, A. S. Cunha, P. Biolac-Sage and C. Perret. "Differential Effects of Inactivated Axin1 and Activated Beta-Catenin Mutations in Human Hepatocellular Carcinomas." *Oncogene* 2007, 26.
4. Cadoret, A., C. Ovejero, B. Terris, E. Souil, L. Levy, W. H. Lamers, J. Kitajewski, A. Kahn and C. Perret. "New Targets of B-Catenin Signaling in the Liver Are Involved in the Glutamine Metabolism." *Oncogene* 2002, 21, 8293-8301.
5. de Lope, C. R., S. Tremosini, A. Forner, M. Reig and J. Bruix. "Management of Liver Diseases 2012management of Hcc." *Journal of Hepatology* 2012, 56, S75-S87.
6. Brosnan, M. E. and J. T. Brosnan. "Hepatic Glutamate Metabolism: A Tale of 2 Hepatocytes." *Am. J Clin. Nut.* 2009, 90, 857S-861S.
7. Wise, D. R. and C. B. Thompson. "Glutamine Addiction: A New Therapeutic Target in Cancer." *Trends in Biochemical Sciences* 2010, 35, 427-433.
8. Medina, M. A. "Glutamine and Cancer." *J Nutr.* 2001, 131, 2539s-2542s.
9. Zigmond, E., A. Ben Ya'acov, H. Lee, Y. Lichtenstein, Z. Shalev, Y. Smith, L. Zolotarov, E. Ziv, R. Kalman, H. V. Le, H. Lu, R. B. Silverman and Y. Ilan. "Suppression of Hepatocellular Carcinoma by Inhibition of Overexpressed Ornithine Aminotransferase." *ACS Med. Chem. Lett.* 2015, 6, 840-844.
10. Miyasaka, Y., N. Enomoto, K. Nagayama, N. Izumi, F. Marumo, M. Watanabe and C. Sato. "Analysis of Differentially Expressed Genes in Human Hepatocellular Carcinoma Using Suppression Subtractive Hybridization." *Brit. J. Cancer* 2001, 85, 228-234.

11. Silverman, R. B. "Design and Mechanism of Gaba Aminotransferase Inactivators. Treatments for Epilepsies and Addictions." *Chem Rev* 2018, 118, 4037-4070.
12. Pan, Y., J. Qiu and R. B. Silverman. "Design, Synthesis, and Biological Activity of a Difluoro-Substituted, Conformationally Rigid Vigabatrin Analogue as a Potent Gamma-Aminobutyric Acid Aminotransferase Inhibitor." *J Med. Chem.* 2003, 46, 5292-5293.
13. Silverman, R. B. "The 2011 E. B. Hershberg Award for Important Discoveries in Medicinally Active Substances: (1s,3s)-3-Amino-4-Difluoromethylenyl-1-Cyclopentanoic Acid (Cpp-115), a Gaba Aminotransferase Inactivator and New Treatment for Drug Addiction and Infantile Spasms." *J. Med. Chem.* 2012, 55, 567-575.
14. Silverman, R. B. "[10] Mechanism-Based Enzyme Inactivators." *Methods in enzymology* 1995, 249, 240-283.
15. Lee, H., E. H. Doud, R. Wu, R. Sanishvili, J. I. Juncosa, D. Liu, N. L. Kelleher and R. B. Silverman. "Mechanism of Inactivation of Gamma-Aminobutyric Acid Aminotransferase by (1s,3s)-3-Amino-4-Difluoromethylene-1-Cyclopentanoic Acid (Cpp-115)." *J. Am. Chem. Soc.* 2015, 137, 2628-2640.
16. Juncosa, J. I., K. Takaya, H. V. Le, M. J. Moschitto, P. M. Weerawarna, R. Mascarenhas, D. Liu, S. L. Dewey and R. B. Silverman. "Design and Mechanism of (S)-3-Amino-4-(Difluoromethylenyl)Cyclopent-1-Ene-1-Carboxylic Acid, a Highly Potent Gamma-Aminobutyric Acid Aminotransferase Inactivator for the Treatment of Addiction." *J Am. Chem. Soc.* 2018, 140, 2151-2164.
17. Liu, W., P. E. Peterson, R. J. Carter, X. Zhou, J. A. Langston, A. J. Fisher and M. D. Toney. "Crystal Structures of Unbound and Aminooxyacetate-Bound *Escherichia Coli* Gamma-Aminobutyrate Aminotransferase." *Biochem.* 2004, 43, 10896-10905.
18. Markova, M., C. Peneff, M. J. Hewlins, T. Schirmer and R. A. John. "Determinants of Substrate Specificity in Omega-Aminotransferases." *J. Biol. Chem.* 2005, 280, 36409-36416.
19. Liu, Y., H. Lai, B. Rong, T. Zhou, J. Hong, C. Yuan, S. Zhao, X. Zhao, B. Jiang and Q. Fang. "Titanium-Mediated Direct Carbon-Carbon Double Bond Formation to A-Trifluoromethyl Acids: A New Contribution to the Knoevenagel Reaction and a High-Yielding and Stereoselective Synthesis of A-Trifluoromethylacrylic Acids." *Adv. Syn. Cat.* 2011, 353, 3161-3165.
20. Ramachandran, P. V., G. Parthasarathy and P. D. Gagare. "Bis-Exo-2-Norbornylboron Triflate for Stereospecific Enolization of 3,3,3-Trifluoropropionates." *Org. Lett.* 2010, 12, 4474-4477.
21. Juncosa, J. I., H. Lee and R. B. Silverman. "Two Continuous Coupled Assays for Omithine-Delta-Aminotransferase." *Anal. Biochem.* 2013, 440, 145-149.
22. Mascarenhas, R., H. V. Le, K. D. Clevenger, H. J. Lehrer, D. Ringe, N. L. Kelleher, R. B. Silverman and D. Liu. "Selective Targeting by a Mechanism-Based Inactivator against Pyridoxal 5'-Phosphate-Dependent Enzymes: Mechanisms of Inactivation and Alternative Turnover." *Biochem.* 2017, 56, 4951-4961.
23. Christensen, E. M., S. M. Patel, D. A. Korasick, A. C. Campbell, K. L. Krause, D. F. Becker and J. J. Tanner. "Resolving the Cofactor Binding Site in the Proline Biosynthetic Enzyme Human Pyrroline-5-Carboxylate Reductase 1." *J. Bio. Chem.* 2017.
24. U.S. Pat. Nos. 8,686,041 and 8,211,865; the contents of which are incorporated herein by reference in their entireties.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound having the following formula or a dissociated form, protonated form, or salt thereof:

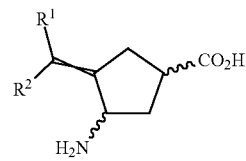

wherein
$R^1$ is hydrogen, alkyl, or haloalkyl; and
$R^2$ is carboxyl, carboxylalkyl ester optionally substituted at one or more positions with halo, carboxylaryl ester, carboxylalkylaryl ester, carboxyl amide, carboxyl-N-alkyl amide, hydroxylalkyl, aminoalkyl, acyl, or cyano.

2. The compound of claim 1, wherein $R^1$ is trifluoromethyl.

3. The compound of claim 1 having a formula:

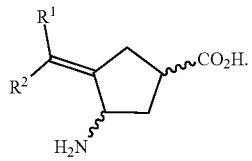

4. The compound of claim 1 having a formula:

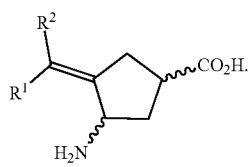

5. The compound of claim 1 having a formula:
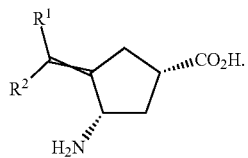
6. The compound of claim 1 having a formula selected from:
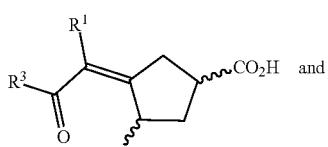
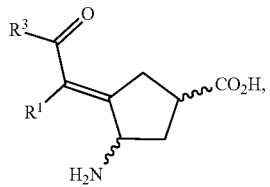
wherein
$R^3$ is hydrogen, hydroxyl, alkyl, alkoxy, phenoxy, arylalkoxy, amino, or alkylamino.
7. The compound of claim 1 having a formula selected from:
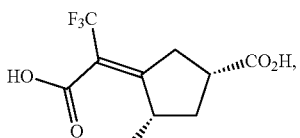
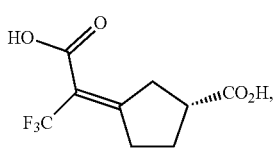
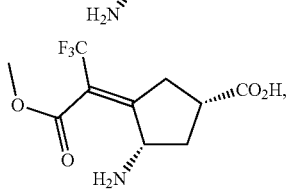
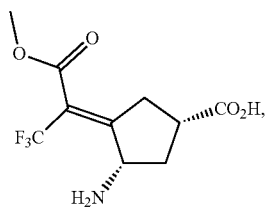
-continued
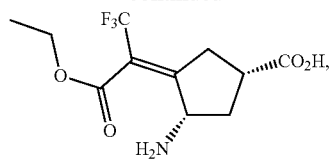
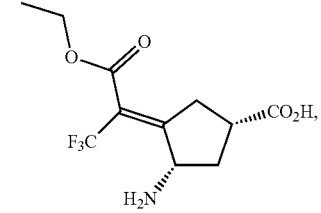
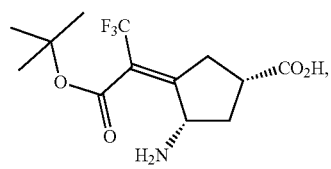
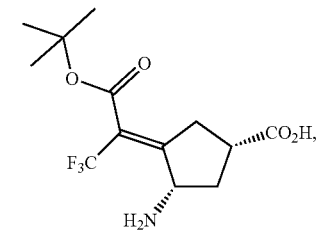
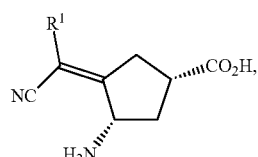
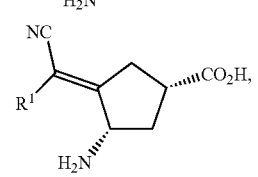
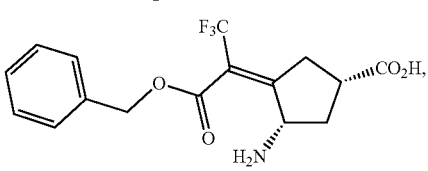
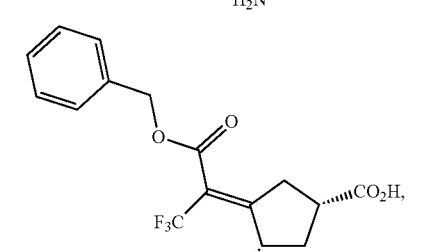
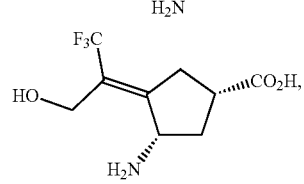

-continued

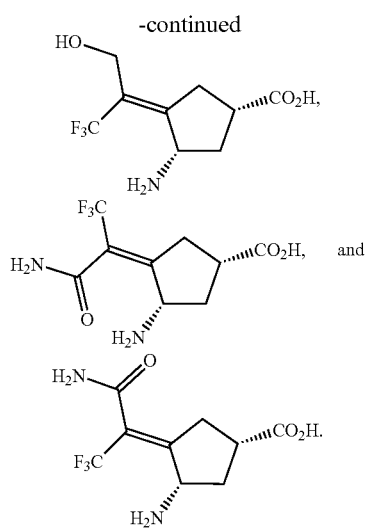

8. A pharmaceutical composition comprising: (i) a compound of claim 1; and (ii) a carrier, excipient, or diluent.

9. The pharmaceutical composition of claim 8, wherein the pharmaceutical composition comprises an effective amount of the compound for treating a disease or disorder associated with ornithine aminotransferase activity.

10. The pharmaceutical composition of claim 8, wherein the pharmaceutical composition comprises an effective amount of the compound for treating a cell proliferative disease or disorder associated with ornithine aminotransferase activity, optionally wherein the cell proliferative disease or disorder is hepatocellular carcinoma.

11. A method for treating a disease or disorder associated with ornithine transferase activity in a subject in need thereof, the method comprising administering to the subject the compound of claim 1.

12. The method of claim 11, wherein the disease or disorder associated with ornithine transferase activity is cancer.

13. The method of claim 11, wherein the disease or disorder associated with ornithine transferase activity is hepatocellular carcinoma.

14. The method of claim 11, wherein the compound is administered orally.

15. The method of claim 11, wherein the compound is administered at a dose that delivers between about 32 mg compound/60 kg subject/day and 200 mg compound/60 kg subject/day.

16. A compound having a formula

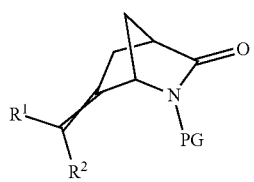

wherein
PG is an amino-protecting group;
$R^1$ is hydrogen, alkyl, or haloalkyl; and
$R^2$ is carboxyl, carboxylalkyl ester optionally substituted at one or more positions with halo, carboxylaryl ester, carboxylalkylaryl ester, carboxyl amide, carboxyl-N-alkyl amide, hydroxylalkyl, aminoalkyl, acyl, or cyano.

17. The compound of claim 16, wherein $R^1$ is trifluoromethyl.

18. The compound of claim 16 having a formula:

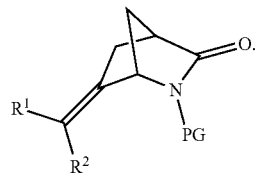

19. The compound of claim 16 having a formula:

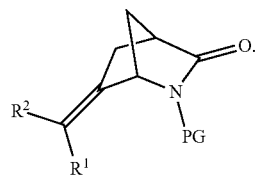

20. The compound of claim 16 having a formula selected from:

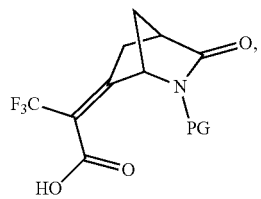

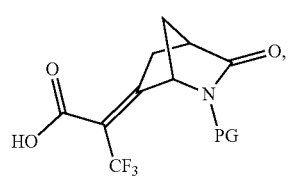

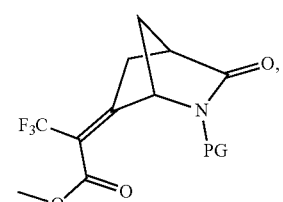

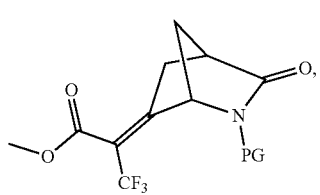

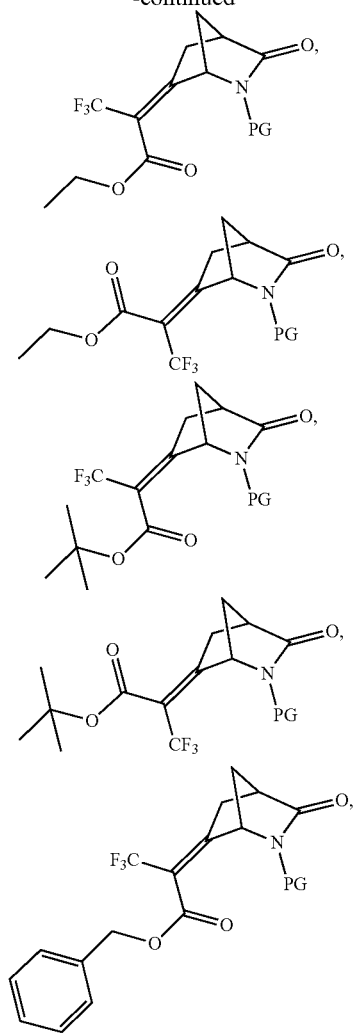
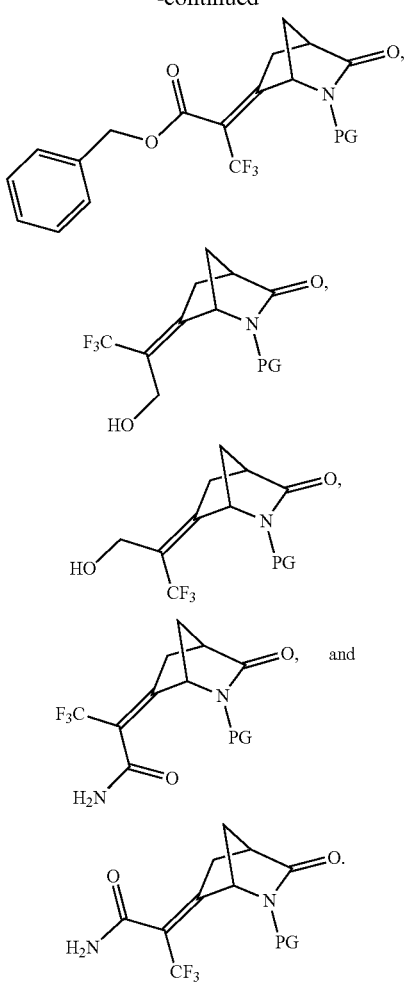
* * * * *